United States Patent
Lee et al.

(10) Patent No.: US 9,849,439 B2
(45) Date of Patent: Dec. 26, 2017

(54) SUPERABSORBENT POLYMER AND PREPARATION METHOD THEREOF

(71) Applicant: LG Chem, Ltd., Seoul (KR)

(72) Inventors: Hyemin Lee, Daejeon (KR); Jin Sook Ryu, Daejeon (KR); Sung Hyun Park, Daejeon (KR); Myung Han Lee, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 14/911,403

(22) PCT Filed: Oct. 7, 2014

(86) PCT No.: PCT/KR2014/009443
§ 371 (c)(1),
(2) Date: Feb. 10, 2016

(87) PCT Pub. No.: WO2015/053538
PCT Pub. Date: Apr. 16, 2015

(65) Prior Publication Data
US 2016/0184799 A1 Jun. 30, 2016

(30) Foreign Application Priority Data
Oct. 7, 2013 (KR) .................. 10-2013-0119037

(51) Int. Cl.
| | | |
|---|---|---|
| B01J 20/26 | (2006.01) | |
| B01J 20/30 | (2006.01) | |
| C08F 2/00 | (2006.01) | |
| C08F 20/10 | (2006.01) | |
| C08J 3/075 | (2006.01) | |
| A61L 15/60 | (2006.01) | |
| C08F 6/00 | (2006.01) | |
| C08L 101/14 | (2006.01) | |
| C08F 6/26 | (2006.01) | |
| C08F 120/06 | (2006.01) | |

(52) U.S. Cl.
CPC .......... B01J 20/267 (2013.01); A61L 15/60 (2013.01); B01J 20/261 (2013.01); B01J 20/3021 (2013.01); B01J 20/3085 (2013.01); C08F 2/00 (2013.01); C08F 6/008 (2013.01); C08F 6/26 (2013.01); C08F 20/10 (2013.01); C08F 120/06 (2013.01); C08L 101/14 (2013.01)

(58) Field of Classification Search
CPC .... C08F 2/00; C08F 6/008; C08F 6/26; C08F 20/10; C08F 120/06; C08L 101/14; B01J 20/261; B01J 20/3021; B01J 20/3085; A61L 15/60
See application file for complete search history.

(56) References Cited

U.S. PATENT DOCUMENTS

| | | |
|---|---|---|
| 5,624,967 A | 4/1997 | Hitomi et al. |
| RE37,021 E | 1/2001 | Aida |
| 2002/0061978 A1 | 5/2002 | Hatsuda et al. |
| 2007/0202772 A1 | 8/2007 | Ikeuchi et al. |
| 2011/0301303 A1 | 12/2011 | Kim et al. |
| 2014/0058048 A1 | 2/2014 | Won et al. |
| 2016/0151531 A1 | 6/2016 | Lee et al. |

FOREIGN PATENT DOCUMENTS

| | | |
|---|---|---|
| CN | 105392805 A | 3/2016 |
| JP | H06-287233 A | 10/1994 |
| JP | H10-182750 A | 7/1998 |
| JP | H11-181005 A | 7/1999 |
| JP | 2003082107 A | 3/2003 |
| JP | 3851915 B2 | 11/2006 |
| KR | 20110049072 A | 5/2011 |
| KR | 20110134333 A | 12/2011 |
| KR | 20120054836 A | 5/2012 |
| KR | 20130017713 A | 2/2013 |
| WO | 2012074254 A2 | 6/2012 |

OTHER PUBLICATIONS

International Search Report for Application No. PCT/KR2014/009443 dated Dec. 10, 2014.
Odian, George, "Principles of Polymerization." Second Edition, 1981, John Wiley & Sons, Inc., p. 203.
Industrial Solvents Handbook, 1996, Marcel Dekker, Inc., pp. 35-68.
Directory of Solvents., 1996, Blackie Academic & Professional, pp. 22-29.
"Hansen Solubility Parameters in Practice." www.Hansen-Solubility.com, 2013.
Cutié, et al., "Size-Exclusion Chromatography of Cross-Linked Superabsorbent Polymers." Journal of Applied Polyjmer Science, vol. 55, 1995, pp. 6059-6609.
Cutié, et al., "Acrylic Acid Polymerization Kinetics." Journal of Polymer Science, Part B: Polymer Physics, vol. 35, 1997, pp. 2029-2047.
Supplementary European Search Report for Application No. EP14852902, dated Feb. 24, 2017.

*Primary Examiner* — Irina S Zemel
*Assistant Examiner* — Jeffrey S Lenihan
(74) *Attorney, Agent, or Firm* — Lerner, David, Littenberg, Krumholz & Mentlik, LLP

(57) ABSTRACT

The present invention relates to a superabsorbent polymer showing a low degree of decrease in absorption capacity, and a preparation method thereof. Specifically, the present invention provides a superabsorbent polymer having an excellent rewetting prevention ability such that moisture hardly leaks out under pressure even after a certain time, and a preparation method thereof, by preparing an acrylic resin with a high molecular weight main chain that is evenly cross-linked for maintaining high gel strength by minimizing an amount of an initiator with respect to a monomer.

9 Claims, No Drawings

SUPERABSORBENT POLYMER AND PREPARATION METHOD THEREOF

CROSS REFERENCE TO RELATED APPLICATIONS

The present application is a national phase entry under 35 U.S.C. §371 of International Application No. PCT/KR2014/009443, filed Oct. 7, 2014, published in Korean, which claims the benefit of Korean Patent Application No. 10-2013-0119037, filed Oct. 7, 2013. The disclosures of said applications are incorporated by reference herein.

TECHNICAL FIELD

The present invention relates to a superabsorbent polymer and a preparation method thereof.

BACKGROUND OF THE INVENTION

A superabsorbent polymer (SAP) is a synthetic polymer material having a function of absorbing water at about 5 hundred times to about 1 thousand times its own weight, and it has been called a superabsorbent material (SAM), an absorbent gel material (AGM), and so on by developing enterprises. The SAP disclosed above initially commercialized for sanitary items and is now being widely used to a water combination soil for horticulture, a water-stop material for civil engineering and construction, a nursery sheet, a freshness preservative in a food distribution field, a poultice material, and the like in addition to the sanitary items like a paper diaper for a child.

The superabsorbent polymer can be prepared through polymerization, drying, pulverization, classification, and surface cross-linking processes. Further, a superabsorbent polymer of which a degree of decrease in absorption capacity is low is advantageous. The degree of decrease in absorption capacity is a value for comparing the absorption speed and the rewetting ability, the absorbed amount during 10 min represents the absorption speed, and the absorbent amount during 3 h means the rewetting prevention ability. When the degree of decrease in absorption capacity is low, absorbed contaminants such as urine do not leak out, and a rash can be prevented.

For this, U.S. Pat. No. 5,624,967 discloses a method of using polyethylene glycol diacrylate (PEGDA) and epoxy resin together as inner cross-linking agents, for preparing an absorbent resin of which the degree of decrease in absorption capacity is low, and it sets the degree of decrease in absorption capacity from 1 to 16. However, examples of the method realize the superabsorbent polymer showing a degree of decrease in absorption capacity of at least about 9, and thus there is a substantial limit in lowering the same. Furthermore, said two or more cross-linking agents including epoxy resin used in the method have difficulty in showing uniform cross-linking distribution in the resin because they have different cross-linking conditions. Moreover, epoxy resin has not recently been used in the preparation of superabsorbent polymers because it is a toxic material.

DETAILS OF THE INVENTION

Objects of the Invention

It is an aspect of the present invention to provide a superabsorbent polymer which not only maintains a high gel strength property of a long chain polymer-polymer network having high molecular weight, and but also shows an excellent ability to prevent rewetting, a phenomenon in which moisture leaks out of the superabsorbent polymer as time passes, and that can prevent a skin rash because of a remarkably low degree of decrease in absorption capacity, and a preparation method thereof.

Means for Achieving the Object

The present invention provides a superabsorbent polymer of which the degree of decrease in absorption capacity represented by the following Calculation Equation 1 is 0 to 1 (g/g).

Degree of decrease in absorption capacity=absorption capacity during 10 min−absorption capacity during 3 h    [Calculation Equation 1]

(In said Calculation Equation 1,
absorption capacity during 10 min is an absorption capacity value of the superabsorbent polymer measured according to the method of the following Calculation Equation 2, and absorption capacity during 3 h is an absorption capacity value of the superabsorbent polymer measured according to the method of the following Calculation Equation 3).

Absorption capacity during 10 min (g/g)=$[B(g)-(C(g))]/(A(g))$    [Calculation Equation 2]

(In Calculation Equation 2,
A is the weight (g) of the superabsorbent polymer,
B is the weight (g) of a nonwoven envelope (85×60 mm) including A (g) of the superabsorbent polymer therein, measured after soaking the same in artificial urine for 10 min, taking it out and draining the same for 5 s in the air, and removing moisture therefrom on 24 sheets of rectangular toilet paper for 10 s, and
C is the weight (g) of a nonwoven envelope not including the superabsorbent polymer, measured after soaking the same in artificial urine for 10 min, taking it out and draining the same for 5 s in the air, and removing moisture therefrom on 24 sheets of rectangular toilet paper for 10 s).

Absorption capacity during 3 h (g/g)=$[B(g)-(C(g))]/(A(g))$    [Calculation Equation 3]

(In Calculation Equation 3,
A is the weight (g) of the superabsorbent polymer,
B is the weight (g) of a nonwoven envelope (85×60 mm) including A (g) of the superabsorbent polymer therein, measured after soaking the same in artificial urine for 3 h, taking it out and draining the same for 5 s in the air, and removing moisture therefrom on 24 sheets of rectangular toilet paper for 10 s, and
C is the weight (g) of a nonwoven envelope not including the superabsorbent polymer, measured after soaking the same in artificial urine for 3 h, taking it out and draining the same for 5 s in the air, and removing moisture therefrom on 24 sheets of rectangular toilet paper for 10 s.)

It is preferable that the superabsorbent polymer includes an acrylic resin of which the weight average molecular weight is 1,500,000 g/mol or more and the gel strength (G') is 7000 Pa or more.

Furthermore, the centrifuge retention capacity (CRC) of the superabsorbent polymer to saline solution, measured according to EDANA method WSP 241.2, may be 20 to 35 g/g, and the content of a water-soluble component thereof may be 0 to 15 wt %.

Meanwhile, the present invention provides a method of preparing the superabsorbent polymer disclosed above, including the steps of:

preparing a monomer composition including a water-soluble ethylenic unsaturated monomer, an inner cross-linking agent, and a polymerization initiator;

preparing a hydrogel polymer by polymerizing said monomer composition in a polymerization reactor;

drying the hydrogel polymer;

pulverizing the dried polymer; and treating the surface of the pulverized polymer, 0.001 to 0.3 parts by weight of the polymerization initiator and 0.2 to 2.0 parts by weight of the inner cross-linking agent are comprised, with respect to 100 parts by weight of the water-soluble ethylenic unsaturated monomer, wherein the step of treating the surface of the polymer includes the step of carrying out a surface cross-linking reaction of the pulverized polymer at 160 to 200° C. for 20 to 60 min by using a surface cross-linking solution including a surface cross-linking agent.

The water-soluble ethylenic unsaturated monomer may include one or more anionic monomers selected from the group consisting of acrylic acid, methacrylic acid, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, and 2-(meth)acrylamide-2-methyl propane sulfonic acid, and salts thereof; one or more nonionic hydrophilic monomers selected from the group consisting of (meth)acrylamide, N-substituted (meth)acrylate, 2-hydroxyethyl(meth)acrylate, 2-hydroxypropyl(meth)acrylate, methoxy polyethylene glycol(meth)acrylate, and polyethylene glycol (meth)acrylate; or one or more amino-containing unsaturated monomers selected from the group consisting of (N,N)-dimethylaminoethyl (meth)acrylate and (N,N)-dimethylaminopropyl (meth)acrylamide, and quaternary compounds thereof.

Furthermore, the inner cross-linking agent may be one or more compounds selected from the group consisting of a $C_8$-$C_{12}$ bisacrylamide, bismethacrylamide, N,N'-methylene bisacrylamide, a poly(meth)acrylate of a $C_2$-$C_{10}$ polyol, a poly(meth)allyl ether of a $C_2$-$C_{10}$ polyol, N,N'-methylene bis(meth)acrylate, ethylene oxy(meth)acrylate, polyethylene oxy(meth)acrylate, propylene oxy(meth)acrylate, glycerin diacrylate, glycerin triacrylate, trimethylolpropane triacrylate, triallylamine, triallyl cyanurate, triallyl isocyanate, polyethylene glycol, diethylene glycol, and propylene glycol.

The polymerization initiator may be any one compound selected from the group consisting of an azo-based initiator, a peroxide-based initiator, a redox-based initiator, an organic halide initiator, a persulfate-based initiator, acetophenone, benzoin, benzophenone, benzyl compounds, and a derivative thereof.

The surface cross-linking agent may be one or more compounds selected from the group consisting of 1,3-propanediol, 2,3,4-trimethyl-1,3-pentanediol, 2-butene-1,4-diol, 1,4-butanediol, 1,3-butanediol, 1,5-pentanediol, 1,6-hexanediol, 1,2-cyclohexanedimethanol, 1,2-hexanediol, 1,3-hexanediol, 2-methyl-1,3-propanediol, 2,5-hexanediol, 2-methyl-1,3-pentanediol, 2-methyl-2,4-pentanediol, ethylene glycol, diethylene glycol, triethylene glycol, tetraethylene glycol, polyethylene glycol, propylene glycol, dipropylene glycol, polypropylene glycol, tripropylene glycol, glycerol, polyglycerol, ethylene carbonate, and 1,2-propylene carbonate.

It is preferable that the surface cross-linking reaction is carried out under the conditions of a maximum reaction temperature of 180 to 200° C., a total reaction time of 0.5 to 1 h, and a reaction temperature of 160° C. or more that are maintained for at least 25 min.

Furthermore, the polymerization may be carried out according to UV polymerization or thermal polymerization. The method may further include the step of pulverizing and classifying the hydrogel polymer into particles having a particle size of 150 to 850 μm after the step of treating the surface of the hydrogel polymer.

Effects of the Invention

The present invention can provide a large molecular weight polymer including a polymer network by using a low but optimal content of an initiator with respect to a monomer so that uniform polymerization and cross-linking occur. Furthermore, the present invention provides a polymer that is superior in a complex property required of a superabsorbent polymer by optimizing the content of the inner cross-linking agent including the base resin in terms of suitable water-soluble components and high gel strength. Therefore, the present invention can provide a superabsorbent polymer suitable for the preparation of comfortable and wearable sanitary items which can prevent a skin rash due to an excellent rewetting prevention ability in which less moisture leaks from the same after a certain time, because the gel strength of the polymer network having a long chain of a high molecular weight is high and the degree of decrease in absorption capacity is a low value of 0 to 1.

DETAILED DESCRIPTION OF THE EMBODIMENT

Hereinafter, the preparation method of the superabsorbent polymer according to a specific embodiment is explained in more detail.

In the superabsorbent polymer, the amount of the water-soluble component increases if the polymer including the polymer network has a low molecular weight of less than 1,500,000 g/mol, and thus the amount of the inner cross-linking agent must be increased for decreasing the same. In this case, CRC decreases and the absorption property falls. Furthermore, even if an optimal surface cross-linking reaction is introduced to the base resin prepared in this way, the initial absorption amount is not maintained for a long time.

Further, even if the molecular weight of the polymer including the polymer network is 1,500,000 g/mol or more, unless specific conditions of the present invention are applied to the surface cross-linking reaction, there is a problem that the initial absorption property is excellent but the gel strength decreases and the initial absorption amount is not maintained for a long time and the polymer is rewetted.

That is, the polymer chain including the polymer network must have a high molecular weight, a uniform cross-linking density, and high gel strength, so that the degree of decrease in absorption capacity is such that it retains moisture absorbed in an early stage for a long time without rewetting. However, existing known polymer resins have not shown uniform cross-linking distribution because the cross-linking agent such as epoxy resin was used.

Therefore, in order for there to be almost no degree of decrease in absorption capacity, the polymer must have a high molecular weight of 1,500,000 g/mol or more and the surface cross-linking reaction at 160 to 200° C. for 20 to 60 min must be applied to the same. As the result, the gel strength thereof can increase and the rewetting phenomenon in which moisture leaks out markedly decreases.

Therefore, the present invention intends to provide a superabsorbent polymer that includes an acrylic resin of an evenly cross-linked network structure and that has a main chain with a high molecular weight, and a preparation method thereof, by minimizing not only the content of the inner cross-linking agent with respect to the monomer, but also the content of the initiator in the polymerization method.

First, according to one embodiment of the invention, a superabsorbent polymer of which the degree of decrease in absorption capacity represented by the following Calculation Equation 1 is 0 to 1 (g/g) is provided.

Degree of decrease in absorption capacity=absorption capacity during 10 min– absorption capacity during 3 h  [Calculation Equation 1]

(In said Calculation Equation 1,
absorption capacity during 10 min is an absorption capacity value of the superabsorbent polymer measured according to the method of the following Calculation Equation 2, and absorption capacity during 3 h is an absorption capacity value of the superabsorbent polymer measured according to the method of the following Calculation Equation 3.)

Absorption capacity during 10 min (g/g)=$[B(g)-(C(g))]/(A(g))$  [Calculation Equation 2]

(In Calculation Equation 2,
A is the weight (g) of the superabsorbent polymer,
B is the weight (g) of a nonwoven envelope (85×60 mm) including A (g) of the superabsorbent polymer therein, measured after soaking the same in artificial urine for 10 min, taking it out and draining the same for 5 s in the air, and removing moisture therefrom on 24 sheets of rectangular toilet paper for 10 s, and
C is the weight (g) of a nonwoven envelope not including the superabsorbent polymer, measured after soaking the same in artificial urine for 10 min, taking it out and draining the same for 5 s in the air, and removing moisture therefrom on 24 sheets of rectangular toilet paper for 10 s).

Absorption capacity during 3 h (g/g)=$[B(g)-(C(g))]/(A(g))$  [Calculation Equation 3]

(In Calculation Equation 3,
A is the weight (g) of the superabsorbent polymer,
B is the weight (g) of a nonwoven envelope (85×60 mm) including A (g) of the superabsorbent polymer therein, measured after soaking the same in artificial urine for 3 h, taking it out and draining the same for 5 s in the air, and removing moisture therefrom on 24 sheets of rectangular toilet paper for 10 s, and
C is the weight (g) of a nonwoven envelope not including the superabsorbent polymer, measured after soaking the same in artificial urine for 3 h, taking it out and draining the same for 5 s in the air, and removing moisture therefrom on 24 sheets of rectangular toilet paper for 10 s.)

At this time, if the degree of decrease in absorption capacity is larger than 1, moisture leaks from the polymer as time passes which may cause a skin rash.

The superabsorbent polymer may include a cross-linked polymer which is prepared by cross-linking the surface of a base resin with a $C_2$-$C_8$ diol or glycol compound. The base resin may be in a powder form that is polymerized by using a water-soluble ethylenic unsaturated monomer including acid groups of which at least parts are neutralized as the inner cross-linking agent.

The superabsorbent polymer of the present invention satisfies the degree of decrease in absorption capacity of less than 1, preferably of 0 to 1, by satisfying a high molecular weight and a specific gel strength range.

Specifically, the weight average molecular weight of the polymer chain including the cross-linking network of the superabsorbent polymer of the present invention may be regulated by the content of the polymerization initiator with respect to the monomer. According to the present invention, it is possible to provide the polymer having the weight average molecular weight of 1,500,000 g/mol or more.

If the molecular weight is less than 1,500,000 g/mol, the base resin including a high content of the water-soluble component is obtained, and thus the resin of which the major properties of the superabsorbent polymer such as absorption ability under pressure or liquid permeability are low is obtained, even if the superabsorbent polymer is obtained through the surface cross-linking reaction of the base resin. When the molecular weight is low, generally, more of the inner cross-linking agent is needed for reducing the content of the water-soluble component. However, in this case, the degree of inner cross-linking increases and high gel strength can be obtained but there is a difficulty in maintaining the absorption ability for a long time. Therefor, the technique for increasing the average molecular weight of the polymer chain by reducing the content of the polymerization initiator is required. However, if the content of the polymerization initiator is too low, the polymerization and cross-linking do not occur evenly and it is difficult for the polymer to gelate, and it is hard for it to function as a superabsorbent polymer because the content of a residual monomer increases.

Therefore, the content of the inner cross-linking agent with respect to the monomer is reduced to a specific range in the present invention so that even polymerization and cross-linking reactions occur in the polymer network. Furthermore, the effects disclosed above can be achieved by using the polymerization initiator of a specific content range that is low but not excessively low.

That is, the present invention can provide the superabsorbent polymer having high gel strength by lowering the content ratio of the polymerization initiator with respect to the monomer to a specific range in order to increase the molecular weight and applying the high temperature surface cross-linking technology of the conditions disclosed above thereto.

Therefore, the superabsorbent polymer of the present invention may have gel strength of 7000 Pa or more, or 7000 Pa to 15,000 Pa.

Furthermore, the superabsorbent polymer obtained by the method of the present invention shows centrifuge retention capacity (CRC) to a saline solution, measured according to EDANA method WSP 241.2, of 20 to 35 g/g, and the content of water-soluble component thereof may be 0 to 15 wt %.

In addition, according to another embodiment of the invention, a method of preparing the superabsorbent polymer disclosed above, including the steps of: preparing a monomer composition including a water-soluble ethylenic unsaturated monomer, an inner cross-linking agent, and a polymerization initiator; preparing a hydrogel polymer by polymerizing said monomer composition in a polymerization reactor; drying the hydrogel polymer; pulverizing the dried polymer; and treating the surface of the pulverized polymer, wherein the step of treating the surface of the polymer includes the step of carrying out a surface cross-linking reaction of the pulverized polymer at 160 to 200° C. for 20 to 60 min by using a surface cross-linking solution including a surface cross-linking agent, is provided.

Specifically, the present invention is characterized in that the content of the polymerization initiator with respect to the monomer and the inner cross-linking agent are optimized together in the preparation method. Therefore, the polymer including the polymer network has a high molecular weight and shows high gel strength because of the increased inner cross-linking and outer cross-linking density, and the superabsorbent polymer having the degree of decrease in absorption capacity of nearly 0 even after a long time can be provided.

Hereinafter, the preparation method of the superabsorbent polymer of the present invention is explained in more detail.

First, the preparation method of the superabsorbent polymer of the present invention includes the processes of polymerization, drying, pulverization, and surface cross-linking.

The base resin is prepared through the processes of polymerization, drying, and pulverization, and the properties of the final superabsorbent polymer may be optimized by the surface cross-linking reaction of the base resin in the surface cross-linking process.

That is, after preparing the monomer composition including a minimum content of the cross-linking agent, the composition is provided to a polymerization reactor and polymerized for preparing the polymer, the polymer is pulverized and classified for preparing the base resin, and the base resin is transferred to a cross-linking reactor after passing through a surface treatment solution. Subsequently, the surface cross-linking reaction is carried out in a surface cross-linking reactor, and the product may be commercialized after classifying the same.

The monomer composition may include a water-soluble ethylenic unsaturated monomer, an inner cross-linking agent, and a polymerization initiator. Furthermore, the polymerization of the monomer composition is preferably carried out in an aqueous solution state.

Any water-soluble ethylenic unsaturated monomer can be used in the present invention without limitation if it is a conventional monomer used in a preparation of a superabsorbent polymer. For example, one or more monomers selected from the group consisting of anionic monomers and salts thereof, nonionic hydrophilic monomers, and amino-containing unsaturated monomers and quaternary compounds thereof may be used.

Specifically, it is preferable that the water-soluble ethylenic unsaturated monomer includes one or more anionic monomers selected from the group consisting of acrylic acid, methacrylic acid, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, and 2-(meth)acrylamide-2-methyl propane sulfonic acid, and salts thereof; one or more nonionic hydrophilic monomers selected from the group consisting of (meth)acrylamide, N-substituted (meth)acrylate, 2-hydroxyethyl(meth)acrylate, 2-hydroxypropyl(meth)acrylate, methoxy polyethylene glycol (meth)acrylate, and polyethylene glycol (meth)acrylate; or one or more amino-containing unsaturated monomers selected from the group consisting of (N,N)-dimethylaminoethyl (meth)acrylate and (N,N)-dimethylaminopropyl (meth)acrylamide; and quaternary compounds thereof. More preferably, the water-soluble ethylenic unsaturated monomer may be acrylic acid or a salt thereof, and it is advantageous in that the properties are superior.

The concentration of the water-soluble ethylenic unsaturated monomer in the monomer composition may be suitably determined by considering the polymerization time and the reaction conditions, and it may preferably be 0.01 to 1.0 wt %. When the concentration of the water-soluble ethylenic unsaturated monomer is less than 0.01 wt %, a high extractable content value may be obtained due to a low cross-linking concentration, and when the concentration is larger than 1.0 wt %, the desired properties may not be obtained because of a high cross-linking concentration.

Furthermore, the inner cross-linking agent is used for adequately regulating the gel strength by controlling the degree of cross-linking of the superabsorbent polymer. The content of the inner cross-linking agent used may preferably be 0.2 to 2 parts by weight, more preferably 0.2 to 1 parts by weight, per 100 parts by weight of the water-soluble ethylenic unsaturated monomer. When the content of the inner cross-linking agent is less than 0.2 parts by weight, the absorption speed and the gel strength of the superabsorbent polymer finally prepared may become weak, and when the content is larger than 2.0 parts by weight, the absorption power of the superabsorbent polymer may be low and it is undesirable for use as an absorbent.

The inner cross-linking agent is not limited as long as it can introduce a cross-linking bond during the polymerization, and a multi-functional cross-linking agent may be solely used or two or more of the same may be used in combination. For example, the inner cross-linking agent may be selected from the group consisting of cross-linking agents including the water-soluble group of the ethylenic unsaturated monomer, at least one functional group which can react with the water-soluble group of the ethylenic unsaturated monomer, and at least one ethylenic unsaturated functional group, or a mixture thereof; and cross-linking agents including the water-soluble group of the ethylenic unsaturated monomer and at least two functional groups which can react with the water-soluble substituent formed by hydrolysis of a vinyl monomer, and a mixture thereof. The inner cross-linking agent may be one or more compounds selected from the group consisting of a $C_8$-$C_{12}$ bisacrylamide, bismethacrylamide, N,N'-methylene bisacrylamide, a poly(meth)acrylate of a $C_2$-$C_{10}$ polyol, poly(meth)allyl ether of a $C_2$-$C_{10}$ polyol, N,N'-methylene bis(meth)acrylate, ethylene oxy(meth)acrylate, polyethylene oxy(meth)acrylate, propylene oxy(meth)acrylate, glycerin diacrylate, glycerin triacrylate, trimethylolpropane triacrylate, triallylamine, triallyl cyanurate, triallyl isocyanate, polyethylene glycol, diethylene glycol, and propylene glycol.

Furthermore, the content of the polymerization initiator may be 0.001 to 0.3 parts by weight, more preferably 0.001 to 0.01 parts by weight, per 100 parts by weight of the monomer. When the content of the initiator is less than 0.001 parts by weight, the polymerization and the cross-linking do not occur evenly and the content of unreacted monomer increases because the content of the initiator is too small. Further, when the content is larger than 0.3 parts by weight, the molecular weight of the polymer including the polymer network becomes small and the number of polymer chains increases. At this time, if the polymer chains are not sufficiently cross-linked, the content of the water-soluble component increases and the properties of the superabsorbent polymer may decrease even if the surface cross-linking reaction is carried out by using the same. Furthermore, when the polymerization is excessively carried out, there may be a problem of not retaining a large amount of moisture for a long time because the superabsorbent polymer becomes stiff and the content of the water-soluble component becomes too small.

As the polymerization initiator, a thermal polymerization initiator or a photo polymerization initiator may be used according to the polymerization method. However, the thermal polymerization initiator may be used in addition when the photopolymerization is applied thereto, because a certain amount of heat is generated by UV radiation and the like even by a photopolymerization reaction, and some heat occurs when the polymerization reaction, which is an exothermic reaction, progresses.

The polymerization initiator may be any one compound selected from the group consisting of an azo-based initiator, a peroxide-based initiator, a redox-based initiator, an organic halide initiator, a persulfate-based initiator, acetophenone, benzoin, benzophenone, benzyl compounds, and a derivative thereof.

Specifically, as examples of azo-based initiators included in the thermal polymerization initiator, there are 2,2-azobis (2-amidinopropane)dihydrochloride, 2,2-azobis-(N,N-dimethylene)isobutyramidine dihydrochloride, 2-(carbamoylazo)isobutyronitrile, 2,2-azobis[2-(2-imidazolin-2-yl) propane] dihydrochloride, 4,4-azobis-(4-cyanovaleric acid), and so on. Furthermore, as examples of persulfate-based initiators, there are sodium persulfate ($Na_2S_2O_8$), potassium persulfate ($K_2S_2O_8$), ammonium persulfate (($NH_4)_2S_2O_8$), and so on. Many more thermal polymerization initiators are disclosed in "Principle of Polymerization (Wiley, 1981)" written by Odian, p. 203, and the present invention is not limited to or by said examples.

In addition, as the polymerization initiator included in the photopolymerization initiator, acetophenone, benzoin, benzophenone, benzyl compounds, or a derivative thereof may be used. For example, one or more photoinitiators selected from the group consisting of acetophenone derivatives such as diethoxy acetophenone, 2-hydroxy-2-methyl-1-phenyl-propane-1-one, benzyl dimethyl tar, 4-(2-hydroxy ethoxy) phenyl-(2-hydroxy)-2-propyl ketone, 1-hydroxycyclohexyl-phenyl ketone, and so on; benzoin alkyl ethers such as benzoin methyl ether, benzoin ethyl ether, benzoin isopropyl ether, and benzoin isobutyl ether; benzophenone derivatives such as methyl o-benzoylbenzoate, 4-phenyl benzophenone, 4-benzoyl-4'-methyl-diphenyl sulfide, (4-benzoyl benzyl)trimethyl ammonium chloride, and so on; thioxanthone-based compounds; acyl phosphine oxide derivatives such as bis(2,4,6-trimethylbenzoyl)-phenyl phosphine oxide, diphenyl(2,4,6-trimethylbenzoyl)-phosphine oxide, and so on; and azo-based compounds such as 2-hydroxy methyl propionitrile, 2,2'[iazobis(2-methyl-N-(1,1'-bis(hydroxymethyl)-2-hydroxyethyl)propionamide)], and so on may be used.

Meanwhile, in the preparation method of the superabsorbent polymer according to one embodiment of the present invention, the base resin can be prepared according to well-known polymerization conditions and drying and pulverizing processes, except that the monomer composition including a specific amount of the polymerization initiator and the inner cross-linking agent is used in the polymerization process.

The conditions for polymerizing the monomer composition are not particularly limited, and any method used in the preparation of common superabsorbent polymers may be used. For example, the polymerization of the monomer composition may be carried out by redox polymerization at the temperature of 30 to 100° C. for 2 to 50 min or thermal or UV polymerization that is carried out at a temperature of 40 to 90° C. for 2 to 30 min. The UV polymerization (photo-polymerization) may be carried out in a wide temperature range of 25 to 99° C. by irradiation with light for 10 s to 5 min because the temperature does not largely influence the UV polymerization. Furthermore, the intensity of the UV radiation may be 0.1 to 30 $mW/cm^2$. The light source and the wavelength range that are well known in the related art can be used in the UV radiation.

Furthermore, in the method of thermal polymerization or UV polymerization of the monomer composition, the polymerization device used is not particularly limited. For example, the thermal polymerization may be generally carried out in a reactor equipped with a stirring spindle, like a kneader, and the UV polymerization (photo-polymerization) may be carried out in a reactor equipped with a continuously moving conveyor belt. However, said polymerization methods are just examples and the present invention is not limited to or by said polymerization methods. In addition, the conveyor belt may be a rotating belt including a rubber, a fabric, a wire mesh, or a plastic resin to which hydrophilicity is slightly imparted.

For example, the hydrogel polymer obtained according to the thermal polymerization that is carried out in the reactor like a kneader equipped with a stirring spindle by providing hot air thereto or heating the reactor may have a particle size of several centimeters to several millimeters when it is discharged from the outlet of the reactor, according to the shape of the stirring spindle equipped in the reactor. Specifically, the size of the obtained hydrogel polymer may vary according to the concentration and the feeding speed of the monomer composition fed thereto, and generally the hydrogel polymer having a particle size of 2 to 50 mm may be obtained.

Further, when the photo-polymerization is carried out by using the reactor equipped with the continuously moving conveyor belt, the hydrogel polymer may be obtained in a sheet form having a width corresponding to a width of the belt. At this time, the thickness of the polymer sheet may vary according to the concentration and the feeding speed of the monomer composition fed thereto, and it is preferable to provide the monomer composition so that a polymer sheet having a thickness of 0.5 to 5 cm is obtained. When the monomer composition is fed so that the thickness of the polymer sheet becomes too thin, it is undesirable because of low production efficiency, and when the thickness of the polymer sheet is over 5 cm, the polymerization reaction may not occur evenly through the thickness because of the excessive thickness.

Preferably, the present invention may prepare the superabsorbent polymer through an apparatus including a monomer feeding part and a thermal polymerization initiator feeding part having separate transfer lines for feeding, and a polymerization reactor connected with the monomer feeding part and the thermal polymerization initiator feeding part for polymerizing the monomer composition including the monomer and the polymerization initiator. At this time, a conventional thermal polymerization initiator may be fed through the polymerization initiator feeding part as necessary, after the monomer and the cross-linking agent are mixed.

The polymerization reactor may also include a means for controlling the temperature of the thermal polymerization reaction inside or outside of the same, and it is preferable to maintain the inner temperature at 60 to 100° C., preferably 90° C.

The temperature and the time for drying the hydrogel polymer may be adequately selected according to the moisture content of the prepared hydrogel polymer, and it may be preferable to carry out the drying process at the temperature of 160 to 180° C. for 20 to 40 min. When the drying temperature is below 160° C., the drying effect is marginal, the drying time grows excessively longer, and it is difficult to make the moisture content be 30 wt % or less. When the drying temperature is higher than 180° C., only the surface of the hydrogel polymer is locally and excessively dried, and many fine particles may be formed in succeeding subsequent pulverizing step.

The device for drying is not particularly limited, and for example, the drying step may be carried out by infrared ray radiation, hot air, microwave radiation, or UV ray radiation. Further, the drying temperature and the time may be adequately selected according to the moisture content of the polymer prepared by the thermal polymerization or UV polymerization, and it may be preferable to carry out the drying process at the temperature of 80 to 200° C. for 20 to 120 min. When the drying temperature is below 80° C., there is a problem in that the drying effect is marginal and the drying time grows excessively longer, while when the drying temperature is higher than 200° C., there is a problem that the SAP is thermal-degraded.

The present invention may further optimize the properties of the superabsorbent polymer by the specific surface treatment process disclosed below, after preparing the base resin including the polymer that is polymerized by using a lower content of the inner cross-linking agent and the polymerization initiator than the existing one and pulverized. That is, the method may include the step of treating the surface of the base resin including the pulverized polymer, and the final superabsorbent polymer may be prepared through the processes disclosed above.

At this time, the surface cross-linking temperature condition applied to the surface treating step is optimized to a specific range of high temperature, and thus the superabsorbent polymer having excellent properties, particularly initial absorptivity and absorption ability in which moisture hardly leaks out under a pressure condition even after a long time, can be prepared. Furthermore, the surface treating method can realize a synergy effect of satisfying a complex property in which all of the properties of the superabsorbent polymer such as centrifuge retention capacity (CRC), absorption ability under pressure (AUP), liquid permeability (SFC), gel strength, and so on are optimized at the same time.

More specifically, the surface cross-linking reaction of the pulverized hydrogel polymer may be carried out by using an aqueous solution including the surface cross-linking agent at a high temperature of 160 to 200° C. for 20 to 60 min. The surface treatment solution may be provided to the hydrogel polymer by a spraying method, but the method is not particularly limited.

According to one embodiment of the present invention, the surface cross-linking agent may include a diol-based compound or a carbonate compound. For example, the surface cross-linking agent may be at least one material selected from the group consisting of materials satisfying $\delta_p$<11 $(J/cm^3)^{1/2}$ and materials satisfying $\delta_H$<4.5$(J/cm^3)^{1/2}$, wherein $\delta_p$ and $\delta_H$ are defined by the Hansen solubility parameter.

For example, the material satisfying $\delta_p$<11 $(J/cm^3)^{1/2}$ may be 1,3-propanediol, 1,6-hexanediol, propylene glycol, 1,2-hexanediol, 1,3-butanediol, 2-methyl-1,3-propanediol, 2,5-hexanediol, 2-methyl-1,3-pentanediol, or 2-methyl-2,4-pentanediol. The material satisfying $\delta_H$<4.5$(J/cm^3)^{1/2}$ may be 1,2-propylenecarbonate. However, the present invention is not limited thereto, and materials not disclosed in Table 1 can also be used if they satisfy the parameter range.

The Hansen solubility parameter, suggested by Charles Hansen, is a method for predicting the case of forming a solution when one material is dissolved in another material. It is disclosed in ¹INDUSTRIAL SOLVENTS HANDBOOK₁ (pp. 35-68, Marcel Dekker, Inc., 1996) or ¹DIRECTORY OF SOLVENTS₁ (pp. 22-29, Blackie Academic & Professional, 1996), for example.

Commonly, the cohesive energy must be calculated initially for calculating the solubility parameter, and the cohesive energy influencing the solubility parameter is classified into three parameters in the Hansen solubility parameter.

$\delta_D$: Solubility parameter caused by non-polar dispersion energy (unit: $(J/cm^3)^{1/2}$)

$\delta_P$: Solubility parameter caused by dipole polar energy (unit: $(J/cm^3)^{1/2}$)

$\delta_H$: Solubility parameter caused by hydrogen bond energy (unit: $(J/cm^3)^{1/2}$)

$\delta_{tot}$: $((\delta_D)^2+(\delta_P)^2+(\delta_H)^2)^{1/2}$

After obtaining the parameters, the similarity of solubility of two materials can be calculated from the difference of Hansen solubility parameters of the two materials. For example, if the Hansen solubility parameter values of two materials A and B are respectively $(\delta_D^A, \delta_P^A, O\delta_H^A)$ and $(\delta_D^B, \delta_P^B, \delta_H^B)$, the difference (Ra) of Hansen solubility parameter values of the two materials can be calculated by the following equation.

$$Ra=(4*(\delta_D^A-\delta_D^B)^2+(\delta_P^A-\delta_P^B)^2+(\delta_H^A-\delta_H^B)^2)^{1/2}$$

The larger the Ra value, lesser the similarity of the two materials in the aspect of solubility.

The Hansen solubility parameter values, calculated by the HSPiP (Hansen Solubility Parameters in Practice, $3^{rd}$ edition version 3.1 published by Hansen-Solubility.com) program developed in the Dr. Hansen group, of several materials which can be used as the cross-linking agent, are as follows.

TABLE 1

| Name of material | Hansen solubility parameter (unit: $(J/cm^3)^{1/2}$) | | | |
| --- | --- | --- | --- | --- |
|  | δD | δP | δH | δtot |
| ethylene glycol | 17 | 11 | 26 | 33 |
| 1,3-propanediol | 16.8 | 13.5 | 23.2 | 31.7 |
| 1,4-butanediol | 16.6 | 11 | 20.9 | 28.9 |
| 1,6-hexanediol | 15.7 | 8.4 | 17.8 | 25.2 |
| propylene glycol | 16.8 | 10.4 | 21.3 | 29.1 |
| 1,2-hexanediol | 16 | 7.4 | 16.7 | 24.9 |
| 1,3-hexanediol | 16.5 | 8.1 | 20.9 | 27.8 |
| 2-methyl-1,3-propanediol | 16.3 | 9.2 | 22.8 | 29.5 |
| 2,5-hexanediol | 16 | 7.5 | 23.9 | 29.7 |
| 2-methyl-1,3-pentanediol | 15.9 | 7.1 | 22.4 | 28.4 |
| 2-methyl-2,4-pentanediol | 16 | 8.3 | 22.1 | 28.5 |
| ethylene carbonate | 18 | 21.7 | 5.1 | 28.7 |
| 1,2-propylene carbonate | 20 | 18 | 4.1 | 27.2 |
| diethylene glycol | 16.6 | 12 | 19 | 27.9 |
| triethylene glycol | 16 | 12.5 | 18.6 | 27.5 |
| tripropylene glycol | 16 | 6.8 | 16.3 | 23.8 |
| glycerol | 17.4 | 11.3 | 27.2 | 34.2 |

The amount of the surface cross-linking agent may be 0.1 to 20 wt % based on the total weight of the surface cross-linking solution.

According to one embodiment of the present invention, the surface cross-linking reaction may be carried out by adding porous silica or clay thereto in addition to the surface cross-linking agent.

The method of adding the surface cross-linking agent to the polymer is not particularly limited. It may be carried out by a method of mixing the surface cross-linking agent and the polymer powder in a reactor, a method of spraying the surface cross-linking agent on the polymer powder, or a method of continuously providing the polymer and the surface cross-linking agent to a mixer that is continuously operated and mixing the same.

When the surface cross-linking agent is added thereto, the surface cross-linking solution may include a mixture of water and one or more alcohols such as methanol. The alcohol may be methanol, normal-propanol, butanol, and so on.

Adding water and methanol has an advantage in that the surface cross-linking agent can be evenly dispersed. At this time, the amount of water and methanol added may be controlled on the basis of 100 parts by weight of the polymer, for the purpose of inducing even dispersion of the surface cross-linking agent, preventing agglomeration of polymer powder, and optimizing surface penetration depth of the cross-linking agent.

The surface cross-linking reaction may be carried out by heating the polymer particles to which the surface cross-linking agent is applied at about 160° C. or more for 20 min or more. Particularly, it is preferable that the surface cross-linking reaction is carried out under the conditions of a maximum reaction temperature of 180 to 200° C., a total reaction time of 0.5 to 1 h, and a reaction temperature of 160° C. or more that is maintained for at least 25 min.

The heating means for the surface cross-linking reaction is not particularly limited. It is possible to provide a thermal media thereto or provide a heat source directly thereto. At this time, usable thermal media may be a heated fluid such as steam, hot air, hot oil, and the like, but the present invention is not limited to or by them. Furthermore, the temperature of the thermal media provided thereto may be properly selected by considering the means of the thermal media, heating speed, and heating target temperature. The heating method for providing the heat source directly thereto may be a heating method using electricity or a heating method using a gas fuel, but the present invention is not limited to or by them.

According to the present invention, the step of pulverizing the dried hydrogel polymer in the process of preparing the base resin may be carried out so that the particle size of the dried hydrogel polymer becomes 150 to 850 µm.

Further, the classification process may be carried out after the pulverization. The classifying step may include the steps of classifying the pulverized hydrogel polymer into 2 grades of a particle size below 150 µm and a particle size of 150 to 850 µm. Furthermore, the pulverized hydrogel polymer may be classified into 2 grades or more in the classifying step as necessary.

In addition, the dried polymer may be further pulverized. At this time, any pulverization method can be used without limitation if it can be used for pulverizing the resin. Preferably, a pulverizing device selected from the group consisting of a pin mill, a hammer mill, a screw mill, a roll mill, and so on may be used. It is preferable that the particle diameter of the final superabsorbent polymer after the pulverizing step is 150 to 850 µm.

The moisture content of the hydrogel polymer of the base resin for the surface treatment is 30 to 60 wt %, but the moisture content of the dried hydrogel polymer obtained through the drying process may be 1 to 10 wt %. At this time, the moisture content of the hydrogel polymer is the content of moisture in the entire weight of the hydrogel polymer, and it means the value of which the weight of the dried polymer is subtracted from the weight of the hydrogel polymer.

The present invention may further include the step of pulverizing and classifying the hydrogel polymer into particles having a particle size of 150 to 850 µm after the surface treatment of the hydrogel polymer.

The superabsorbent polymer prepared by the method disclosed above is characterized in that the polymer chain including the polymer network has a high molecular weight, the cross-linking density thereof is even, the polymer shows high gel strength, and the degree of decrease in absorption capacity of the same is very low compared to existing polymers. Furthermore, the present invention provides the superabsorbent polymer that is hardly rewetted by absorbed moisture because of a high degree of inner and outer cross-linking in the main chain of a high molecular weight.

Therefore, the superabsorbent polymer of the present invention can show excellent properties, particularly initial absorptivity and absorption ability in which moisture hardly leaks out under a pressured condition even after a long time. Accordingly, the superabsorbent polymer satisfying the specific parameter properties of the present invention can be widely used as a water combination soil for horticulture, a water-stop material for civil engineering and construction, a nursery sheet, a freshness preservative in a food distribution field, a poultice material, and the like in addition to various sanitary applications.

Hereinafter, the action and the effect of the present invention are explained in more detail through specific examples of the invention. However, the following examples are only for illustrating the present invention, and the scope of a right of the invention is not limited to or by them.

Example 1

After 500 g of acrylic acid and 4 g of N,N'-methylene bisacrylamide, the inner cross-linking agent, were mixed, 0.01 g of diphenyl(2,4,6-trimethylbenzoyl)-phosphine oxide, the polymerization initiator, was added thereto and dissolved therein. Subsequently, the water-soluble unsaturated monomer aqueous solution was prepared by adding 896.4 g of a sodium hydroxide solution at a concentration of 24.5 wt % thereto while continuously feeding nitrogen. The hydrogel polymer was obtained by cooling the solution to 60° C. and exposing the aqueous solution to UV rays for 90 s. The obtained hydrogel polymer was pulverized and dried at a temperature of 180° C. for 30 min by using a hot air drier, and the dried hydrogel polymer was pulverized by using a pulverizer. Thereafter, the base resin powder having a particle size of 150 to 850 µm was obtained by classifying the same with an ASTM standard sieve.

The surface treatment solution including 5 wt % of 1,3-propanediol and 5 wt % of propylene glycol was sprayed on the classified base resin powder, and the base resin and the surface cross-linking solution were mixed. After providing the polymer mixed with the cross-linking solution to a surface cross-linking reactor, the surface cross-linking reaction of the hydrogel polymer was carried out at a temperature of 185° C. for 40 min.

After the surface cross-linking reaction, the superabsorbent polymer having the particle size of 150 to 850 µm was obtained by classifying the same with an ASTM standard sieve.

Example 2

The superabsorbent polymer was obtained according to the same method as in Example 1, except that 0.02 g of diphenyl(2,4,6-trimethylbenzoyl)-phosphine oxide, the polymerization initiator, and 1.1 g of N,N'-methylene bisacrylamide, the inner cross-linking agent, were used.

Comparative Example 1

The superabsorbent polymer was obtained according to the same method as in Example 1, except that 1.65 g of diphenyl(2,4,6-trimethylbenzoyl)-phosphine oxide, the polymerization initiator, and 11.5 g of N,N'-methylene bisacrylamide, the inner cross-linking agent, were used.

Comparative Example 2

The base resin was obtained according to the same method as in Example 1, except that 2 g of diphenyl(2,4,6-trimethylbenzoyl)-phosphine oxide, the polymerization initiator, and 1.1 g of N,N'-methylene bisacrylamide, the inner cross-linking agent, were used.

The surface treatment solution including 0.3 wt % of ethylene glycol diglycidyl ether was sprayed on the classified base resin, and the base resin and the surface cross-linking solution were mixed. After providing the polymer mixed with the cross-linking solution to a surface cross-linking reactor, a surface cross-linking reaction of the hydrogel polymer was carried out at a temperature of 140° C. for 40 min. After the surface cross-linking reaction, the superabsorbent polymer having the particle size of 150 to 850 μm was obtained by classifying the same with an ASTM standard sieve.

Comparative Example 3

The base resin was obtained according to the same method as in Example 1, except that 0.1 g of diphenyl(2,4,6-trimethylbenzoyl)-phosphine oxide, the polymerization initiator, and 0.7 g of N,N'-methylene bisacrylamide, the inner cross-linking agent, were used. Then, the superabsorbent polymer was obtained by carrying out the surface cross-linking reaction according to the same method as in Comparative Example 2.

Comparative Example 4

The base resin was obtained according to the same method as in Example 1, except that 2 g of diphenyl(2,4,6-trimethylbenzoyl)-phosphine oxide, the polymerization initiator, and 7.5 g of N,N'-methylene bisacrylamide, the inner cross-linking agent, were used. Then, the superabsorbent polymer was obtained by carrying out the surface cross-linking reaction according to the same method as in Comparative Example 2.

Comparative Example 5

The base resin was obtained according to the same method as in Example 2, and the superabsorbent polymer was then obtained by carrying out the surface cross-linking reaction according to the same method as in Comparative Example 2.

Experimental Examples

Evaluation on the Properties of the Superabsorbent Polymers (1) Weight Average Molecular Weight First, the cross-linking point of the superabsorbent polymer was artificially cut and linear chains of the same were sampled for measuring the weight average molecular weight of the polymer. The pretreatment method of the superabsorbent polymer referred to in the literature (*J. applied polymer science* 1995, 55, 605-609, *Journal of Polymer Science: Part B: Polymer Physics*, 1997, 35, 2029-2047). After putting 0.4 g of the superabsorbent polymer in 1 N NaOH (100 ml) and adding 0.4 g of MEHQ thereto, the mixture was stored in an oven of 75° C. for 7 d so that a hydrolysis reaction progressed. After the hydrolysis reaction, the specimen was diluted with a GPC solvent (0.1 M NaNO3+pH 7.0 phosphate buffer) to a concentration of about 0.8 mg/mL. The GPC column used in the analysis was Waters ultrahydrogel linear×2, the temperature in the column was 40° C., and the fluid speed was regulated to 1.0 mL/min. The detector used was an RI detector. After the apparatus was stabilized, standards materials (7 kinds of poly(acrylic acid)) and the specimen for measurement were put therein and the weight average molecular weight thereof was measured.

(2) Degree of Decrease in Absorption Capacity

In the present invention, the degree of decrease in absorption capacity means the value measured by the following method.

After putting "A" g (about 0.2 g) of the superabsorbent polymer in a nonwoven envelope (85×60 mm), the envelope was soaked in artificial urine (an aqueous solution in which 1.9 wt % of urea, 0.8 wt % of sodium chloride, 0.1 wt % of magnesium sulfate, and 0.1 wt % of calcium chloride were dissolved) at 25° C. After the lapse of time, the nonwoven envelope was taken out and drained for 5 s in the air, moisture was removed therefrom on 24 sheets of rectangular toilet paper for 10 s, and then the weight ("B" g) of the same was measured. The weight ("C" g) of the nonwoven envelope not including the superabsorbent polymer was measured according to the same method disclosed above, and the #3 was measured by the following Calculation Equations 1 to 3.

Degree of decrease in absorption capacity=absorption capacity during 10 min− absorption capacity during 3 h.    [Calculation Equation 1]

(In said Calculation Equation 1, absorption capacity during 10 min is an absorption capacity value of the superabsorbent polymer measured according to the method of the following Calculation Equation 2, and absorption capacity during 3 h is an absorption capacity value of the superabsorbent polymer measured according to the method of the following Calculation Equation 3.)

Absorption capacity during 10 min (g/g)=[B(g)−(C(g))]/(A(g))    [Calculation Equation 2]

(In Calculation Equation 2,
A is the weight (g) of the superabsorbent polymer,
B is the weight (g) of a nonwoven envelope (85×60 mm) including A (g) of the superabsorbent polymer therein, measured after soaking the same in artificial urine for 10 min, taking it out and draining the same for 5 s in the air, and removing moisture therefrom on 24 sheets of rectangular toilet paper for 10 s, and
C is the weight (g) of a nonwoven envelope not including the superabsorbent polymer, measured after soaking the same in artificial urine for 10 min, taking it out and draining the same for 5 s in the air, and removing moisture therefrom on 24 sheets of rectangular toilet paper for 10 s.)

Absorption capacity during 3 h (g/g)=[B(g)−(C(g))]/(A(g))    [Calculation Equation 3]

(In Calculation Equation 3,
A is the weight (g) of the superabsorbent polymer,
B is the weight (g) of a nonwoven envelope (85×60 mm) including A (g) of the superabsorbent polymer therein, measured after soaking the same in artificial urine for 3 h, taking it out and draining the same for 5 s in the air, and removing moisture therefrom on 24 sheets of rectangular toilet paper for 10 s, and C is the weight (g) of a nonwoven envelope not including the superabsorbent polymer, measured after soaking the same in artificial urine for 3 h, taking it out and draining the same for 5 s in the air, and removing moisture therefrom on 24 sheets of rectangular toilet paper for 10 s.)

(3) Absorption Capacity Under Non-Loading Condition (CRC, Centrifuge Retention Capacity)

To the superabsorbent polymers of the examples and comparative examples, the centrifuge retention capacity (CRC) by absorption capacity under a non-loading condition was measured according to EDANA method WSP 241.2.

That is, after uniformly inserting W (g) (about 0.2 g) of each polymer obtained in the examples and comparative examples in a nonwoven envelope and sealing the same, it was soaked in a 0.9 wt % saline solution at room temperature for 30 min. After dehydrating the same by using a centrifuge at 250 G for 3 min, the weight W2 (g) of the envelope was measured. Further, after carrying out the same operation without using the resin, the weight W1 (g) of the envelope was measured. CRC (g/g) was calculated by using the obtained weight values according to the following equation.

$$CRC(g/g) = \{(W2(g) - W1(g) - W(g))\}/W(g)\}$$ [Calculation Equation 4]

(In Calculation Equation 4,

W (g) is the weight (g) of the superabsorbent polymer,

W1 (g) is the weight of the nonwoven envelope not including the superabsorbent polymer, measured after soaking the same in a 0.9 wt % saline solution at room temperature for 30 min and dehydrating the same by using a centrifuge at 250 G for 3 min, and W2 (g) is the weight of the nonwoven envelope including the superabsorbent polymer, measured after soaking the same in a 0.9 wt % saline solution at room temperature for 30 min and dehydrating the same by using a centrifuge at 250 G for 3 min.)

(4) Water-Soluble Component (Extractable Content)

The water-soluble component (extractable content) was measured according to the same order and method as disclosed in EDANA method WSP 270.2.

(5) G' Measurement (Gel Strength)

The gel strength (G') of the superabsorbent polymers was measured by using a rheometer according to the following order.

The superabsorbent polymer was soaked in an excess amount (100 times or more of the polymer) of a 0.9 wt % NaCl solution for 1 h. The solvent not absorbed therein was removed by using an aspirator for 4 min, and the solvent left on the surface of the same was evenly distributed and wiped once with a filter paper. 2.5 g of the swelled superabsorbent polymer was loaded between two plates (parallel plates with a 25 mm diameter, a lower plate thereof having a wall with a 2 mm height for preventing the sample from leaking) of the rheometer, and the gap (1 mm) between the plates was adjusted. At this time, if too small an amount of the swelled polymer is loaded, the gel strength may be measured low because the gap between the plates is not perfectly packed. Furthermore, it is generally easy to adjust the gap to 1 mm with a soft sample, but a hard sample needs a lot of force in the vertical direction of the plate for adjusting the gap to 1 mm. Therefore, the gap was properly adjusted by pressing the plates with a force of 3 N so that the swelled sample contacted evenly at the face of the plates. The sample was stabilized during 5 min of rest time because the force was provided to the swelled polymer. A linear viscoelastic regime section of strain where the storage modulus (G') and the loss modulus (G") were steady was found by using the rheometer while increasing the strain at a 10 rad/s frequency. Generally, in the case of a swelled superabsorbent polymer, a strain of 0.1% is imparted in the liner regime section. The viscoelasticity (G', G") of the swelled polymer was measured by using the strain value of the linear regime section at a constant frequency of 10 rad/s for 60 s. The gel strength (G') was obtained by taking an average of the obtained G' values.

TABLE 2

| | CRC (g/g) | Extractable content (%) | G' (Pa) | Mw (g/mol) | Absorption capacity | | Degree of decrease in absorption capacity |
|---|---|---|---|---|---|---|---|
| | | | | | 10 min | 3 h | |
| Example 1 | 29.5 | 7.9 | 7800 | 1.66E+06 | 23.93 | 23.92 | 0.01 |
| Example 2 | 33 | 11 | 7200 | 1.59E+06 | 26.14 | 26.06 | 0.08 |
| Comparative Example 1 | 29.7 | 12 | 8770 | 1.4E+06 | 24.76 | 23.52 | 1.24 |
| Comparative Example 2 | 41 | 29.6 | 2500 | 5.98E+05 | 44.17 | 34.03 | 10.14 |
| Comparative Example 3 | 44 | 23.4 | 3000 | 1.56E+06 | 42.72 | 33.21 | 9.51 |
| Comparative Example 4 | 34.2 | 15.3 | 5400 | 8.96E+05 | 41.02 | 31.56 | 9.46 |
| Comparative Example 5 | 34.7 | 10.7 | 6700 | 1.59E+06 | 36.56 | 26.60 | 9.77 |

As shown in the results of Table 2, it is recognizable that the examples of the present invention show a very low degree of decrease in absorption capacity and can provide the superabsorbent polymer having excellent properties, compared to the comparative examples. Furthermore, it is shown that if the polymer does not satisfy both the molecular weight of 1,500,000 g/mol or more and the gel strength value of 7000 or more, the degree of decrease in absorption capacity is undesirably high.

The invention claimed is:

1. A superabsorbent polymer prepared by a method comprising:
preparing a hydrogel polymer by polymerizing a water-soluble ethylenic unsaturated monomer, in the presence of a sole inner cross-linking agent and a polymerization initiators;
drying the hydrogel polymer;
pulverizing the dried polymer; and
treating the surface of the pulverized polymer,
wherein 0.001 to 0.01 parts by weight of the polymerization initiator and 0.2 to 2.0 parts by weight of the inner cross-linking agent are comprised, with respect to 100 parts by weight of the water-soluble ethylenic unsaturated monomer, wherein the step of treating the surface of the polymer includes the step of carrying out a surface cross-linking reaction of the pulverized polymer at 160 to 200° C. for 20 to 60 min by using a surface cross-linking solution including a surface cross-linking agent, wherein the water-soluble ethylenic unsaturated monomer includes one or more anionic monomers selected from the group consisting of maleic anhydride, fumaric acid, itaconic acid, 2-acryloyl ethane sulfonic acid, 2-methacryloyl ethane sulfonic acid, 2-(meth)acryloyl propane sulfonic acid, and 2-(meth)acrylamide-2-methyl propane sulfonic acid, and salts thereof; one or more nonionic hydrophilic monomers selected from the group consisting of (meth)acrylamide, N-substituted (meth)acrylate, 2-hydroxyethyl(meth)acrylate, 2-hydroxypropyl(meth)acrylate, methoxy polyethylene glycol(meth)acrylate, and polyethylene glycol (meth)acrylate; or one or more amino-containing unsaturated monomers selected from the group consisting of (N,N)-dimethylaminoethyl (meth)acrylate and (N,N)-dimethylaminopropyl (meth)acrylamide, and quaternary compounds thereof, wherein the inner cross-linking agent is one or more compounds selected from the group consisting of a C8-C12 bisacrylamide, bismethacrylamide, N,N'-methylene bisacrylamide, a poly(meth)acrylate of a C2-C10 polyol, a poly(meth)allyl ether of a C2-C10 polyol, N,N'-methylene bis(meth)acrylate, ethylene oxy(meth)acrylate, polyethylene oxy(meth)acrylate, propylene oxy(meth)acrylate, glycerin diacrylate, glycerin triacrylate, trimethylolpropane triacrylate, triallylamine, triallyl cyanurate, triallyl isocyanate, polyethylene glycol, diethylene glycol, and propylene glycol, and wherein the superabsorbent polymer has a degree of decrease in absorption capacity represented by the following Calculation Equation 1 is 0 to 1 (g/g):

Degree of decrease in absorption capacity=absorption capacity during 10 min−absorption capacity during 3 h [Calculation Equation 1]

(in said Calculation Equation 1, absorption capacity during 10 min is an absorption capacity value of the superabsorbent polymer measured according to the method of the following Calculation Equation 2, and absorption capacity during 3 h is an absorption capacity value of the superabsorbent polymer measured according to the method of the following Calculation Equation 3), Absorption capacity during 10 min (g/g)=[$B$(g)−($C$(g))]/($A$(g)) [Calculation Equation 2]

(in Calculation Equation 2,

A is the weight (g) of the superabsorbent polymer,

B is the weight (g) of a nonwoven envelope (85×60 mm) including A (g) of the superabsorbent polymer therein, measured after soaking the same in artificial urine for 10 min, taking it out and draining the same for 5 s in the air, and removing moisture therefrom on 24 sheets of rectangular toilet paper for 10 s, and C is the weight (g) of a nonwoven envelope not including the superabsorbent polymer, measured after soaking the same in artificial urine for 10 min, taking it out and draining the same for 5 s in the air, and removing moisture therefrom on 24 sheets of rectangular toilet paper for 10 s), and Absorption capacity during 3 h (g/g)=[$B$(g)−($C$(g))]/($A$(g)) [Calculation Equation 3]

(in Calculation Equation 3,

A is the weight (g) of the superabsorbent polymer,

B is the weight (g) of a nonwoven envelope (85×60 mm) including A (g) of the superabsorbent polymer therein, measured after soaking the same in artificial urine for 3 h, taking it out and draining the same for 5 s in the air, and removing moisture therefrom on 24 sheets of rectangular toilet paper for 10 s, and C is the weight (g) of the nonwoven envelope not including the superabsorbent polymer, measured after soaking the same in artificial urine for 3 h, taking it out and draining the same for 5 s in the air, and removing moisture therefrom on 24 sheets of rectangular toilet paper for 10 s).

2. The superabsorbent polymer according to claim 1, wherein the superabsorbent polymer comprises an acrylic resin having a weight average molecular weight is 1,500,000 g/mol or more and gel strength (G') is 7000 Pa or more.

3. The superabsorbent polymer according to claim 1, wherein the superabsorbent polymer has a centrifuge retention capacity (CRC) to a saline solution, measured according to EDANA method WSP 241.2, is 20 to 35 g/g, and a content of a water-soluble component is 0 to 15 wt %.

4. A method of preparing a superabsorbent polymer, including the steps of:

preparing a hydrogel polymer by polymerizing a water-soluble ethylenic unsaturated monomer, in the presence of a sole inner cross-linking agent and a polymerization initiators;

drying the hydrogel polymer;

pulverizing the dried polymer; and treating the surface of the pulverized polymer, 0.001 to 0.01 parts by weight of the polymerization initiator and 0.2 to 2.0 parts by weight of the inner cross-linking agent are comprised, with respect to 100 parts by weight of the water-soluble ethylenic unsaturated monomer, wherein the step of treating the surface of the polymer includes the step of carrying out a surface cross-linking reaction of the pulverized polymer at 160 to 200° C. for 20 to 60 min by using a surface cross-linking solution including a surface cross-linking agent, wherein the water-soluble ethylenic unsaturated monomer includes one or more anionic monomers selected from the group consisting of maleic anhydride, fumaric acid, itaconic acid, 2-acryloyl ethane sulfonic acid, 2-methacryloyl ethane sulfonic acid, 2-(meth)acryloyl propane sulfonic acid, and 2-(meth)acrylamide-2-methyl propane sulfonic acid, and salts thereof; one or more nonionic hydrophilic monomers selected from the group consisting of (meth)acrylamide, N-substituted (meth)acrylate, 2-hydroxyethyl(meth)acrylate, 2-hydroxypropyl(meth)acrylate, methoxy polyethylene glycol(meth)acrylate, and polyethylene glycol (meth)acrylate; or one or more amino-containing unsaturated monomers selected from the group consisting of (N,N)-dimethylaminoethyl (meth)acrylate and (N,N)-dimethylaminopropyl (meth)acrylamide, and quaternary compounds thereof, and wherein the inner cross-linking agent is one or more compounds selected from the group consisting of a C8-C12 bisacrylamide, bismethacrylamide, N,N'-methylene bisacrylamide, a poly(meth)acrylate of a C2-C10 polyol, a poly(meth)allyl ether of a C2-C10 polyol, N,N'-methylene bis(meth)acrylate, ethylene oxy(meth)acrylate, polyethylene oxy(meth)acrylate, propylene oxy(meth)acrylate, glycerin diacrylate, glycerin triacrylate, trimethylolpropane triacrylate, triallylamine, triallyl cyanurate, triallyl isocyanate, polyethylene glycol, diethylene glycol, and propylene glycol.

5. The method according to claim 4, wherein the polymerization initiator is any one compound selected from the group consisting of an azo-based initiator, a peroxide-based initiator, a redox-based initiator, an organic halide initiator, a persulfate-based initiator, acetophenone, benzoin, benzophenone, benzyl compounds, and a derivative thereof.

6. The method according to claim 4, wherein the surface cross-linking agent is one or more compounds selected from the group consisting of 1,3-propanediol, 2,3,4-trimethyl-1,3-pentanediol, 2-butene-1,4-diol, 1,4-butanediol, 1,3-butanediol, 1,5-pentanediol, 1,6-hexanediol, 1,2-cyclohexanedimethanol, 1,2-hexanediol, 1,3-hexanediol, 2-methyl-1,3-propanediol, 2,5-hexanediol, 2-methyl-1,3-pentanediol, 2-methyl-2,4-pentanediol, ethylene glycol, diethylene glycol, triethylene glycol, tetraethylene glycol, polyethylene glycol, propylene glycol, dipropylene glycol, polypropylene glycol, tripropylene glycol, glycerol, polyglycerol, ethylene carbonate, and 1,2-propylene carbonate.

7. The method according to claim 4, wherein the surface cross-linking reaction is carried out under the conditions of a maximum reaction temperature of 180 to 200° C., a total reaction time of 0.5 to 1 h, and a reaction temperature of 160° C. or more that is maintained for at least 25 min.

8. The method according to claim 4, wherein the polymerization is carried out according to UV polymerization or thermal polymerization.

9. The method according to claim 4, further including the step of pulverizing and classifying the hydrogel polymer into particles having a particle size of 150 to 850 μm after the step of treating the surface of the hydrogel polymer.

* * * * *